United States Patent [19]

Hrebeniuk

[11] Patent Number: Plant 6,852

[45] Date of Patent: Jun. 13, 1989

[54] DISTINCT VARIETY OF POINSETTIA NAMED H516A

[76] Inventor: Alexander Hrebeniuk, R.D. #1, Box 118, Sugar Run, Pa. 18846

[21] Appl. No.: 178,332

[22] Filed: Apr. 6, 1988

[51] Int. Cl.[4] ..... A01H 5/00

[52] U.S. Cl. ..... Plt./86

[58] Field of Search ..... Plt./86

*Primary Examiner*—James R. Feyrer

*Attorney, Agent, or Firm*—Webb, Burden, Ziesenheim & Webb

[57] ABSTRACT

A Poinsettia plant named H516A, particularly characterized by the combined characteristics of dark red and fade resistance bracts, dark green foliage, triple form and compact habit, large bracts, tight and long lasting Cyathia and long lasting keeping qualities, and parts therefor.

1 Drawing Sheet

BACKGROUND OF THE NEW PLANT

The present invention comprises a new and distinct cultivar of *Euphorbia pulcherrima* known by the varietal name H516A. The new cultivar was developed in a breeding program and is a seedling resulting from the cross of the seed parent H518 Dynasty (Plant Patent pending) and the pollen parent H52-V18.

The new cultivar was discovered in November of 1986 in Sugar Run, Pa.; was first asexually reproduced by cuttings in May of 1987 in Sugar Run, Pa. and has been repeatedly asexually reproduced by cuttings at Sugar Run, Pa. Continued observations of the vegetative cuttings have confirmed that the distinguishing features of this new cultivar come true, remain stable and are retained through successive propagations.

The following traits are determined to be basic characteristics of this new cultivar which in combination distinguish this Poinsettia as new and distinct:

1. Nine to nine-and-one-half week response time under black cloth.
2. Four to six breaks after pinch.
3. May be grown single stem or pinch.
4. Top leaves are very dark green.
5. Mature leaves are also dark green.
6. Petioles are very dark red, shiny and waxy.
7. Veins in leaves are reddish on top rows and are a lighter green on the lower rows.
8. Stems are greenish-red, shiny and waxy.
9. Bracts are bright dark red and fade resistant in the glasshouse, plastic house and home.
10. The centers of the bloom are very tight; Cyathia stay on to six weeks.
11. The full bloom has three rows of bracts.
12. Twenty-two bracts have been counted on a fully developed bloom.
13. The largest bloom size measured on a single stem plant is 20 inches in diameter.
14. Bracts range in size from 5 cm to 11.5 cm wide and 8 to 20 cm long.
15. In normal blooming, the cultivar shows color by the beginning of November and the bracts are fully developed by December.
16. Responds well to the growth regulator Cycocel.
17. Plants ship well and are long lasting and keep well in the home.

18. Ability to grow at temperatures of 65° F.; when fully bloomed, flower retains its beauty and light at a temperature of 60° F. and has non-drooping foliage.

DESCRIPTION OF THE DRAWING

The accompanying photographic drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out in Sugar Run, Pa. The plant history was taken on nine and one-half week plants. The color readings were determined at 12:30 p.m. on Feb. 3, 1988 under natural daylight at Sugar Run, Pa. Color references are primarily to the R.H.S. Colour Chart of The Royal Horticultural Society of London.

The plant:

*Form.*—Triple.

*Growth habit.*—Compact; medium growth.

*Rooting.*—Very uniform and very fast.

*Blooming season.*—Nine and one-half weeks.

*Blooming habit.*—Large bracts in triple rows; compact.

Foliage:

*Size.*—8 to 10 cm. wide and 12 to 14 cm. long.

*Quantity.*—Up to twelve leaves per stem depending on culture.

*Color.*—New foliage — Upper side, Green Group 139A. Under side, Green Group 139B. Old foliage — Upper side, Green Group 139A. Under side, Green Group 139B. Leaf petiole — Red Group 53A.

*Shape.*—Generally heart shaped, some generally oak shaped.

*Texture.*—The upper side is velvety smooth; top row leaves have red veins while lower row leaves have veins of lighter green; under side leaves are rough because of veins; veins are light green; midrib is red and pinkish.

*Edge of margin.*—Wavy.

*Veins.*—Midrib to margin.

*Disease resistance.*—Very resistant to Botrytis.

Flower: Cyathia.

*Borne.*—Single, very tight compact inflorescence.

*Quantity.*—No more than 12; each one has a nectary.

*Color.*—Varies widely depending on stage of development; generally orange to orange-red when mature.

Bracts:

*Size.*—5 cm. wide and 8 cm. long when immature; up to 11.5 cm. wide and 20 cm. long when fully grown.

*Veins.*—Midrib to margin.

*Quantity.*—24 bracts have been counted on a fully developed bloom.

*Color.*—Top: Red Group 53 B. Bottom: Red Group 53 C.

*Resistance to fade.*—Excellent, long lasting.

Reproductive organs: Typical for poinsettia cultivars.

I claim:

1. A new and distinct variety of Poinsettia plant as herein shown and described and particularly characterized by its dark red and fade resistance bracts, dark green foliage, triple form and compact habit, large bracts, tight and long lasting Cyathia and long lasting keeping qualities, and parts therefor.

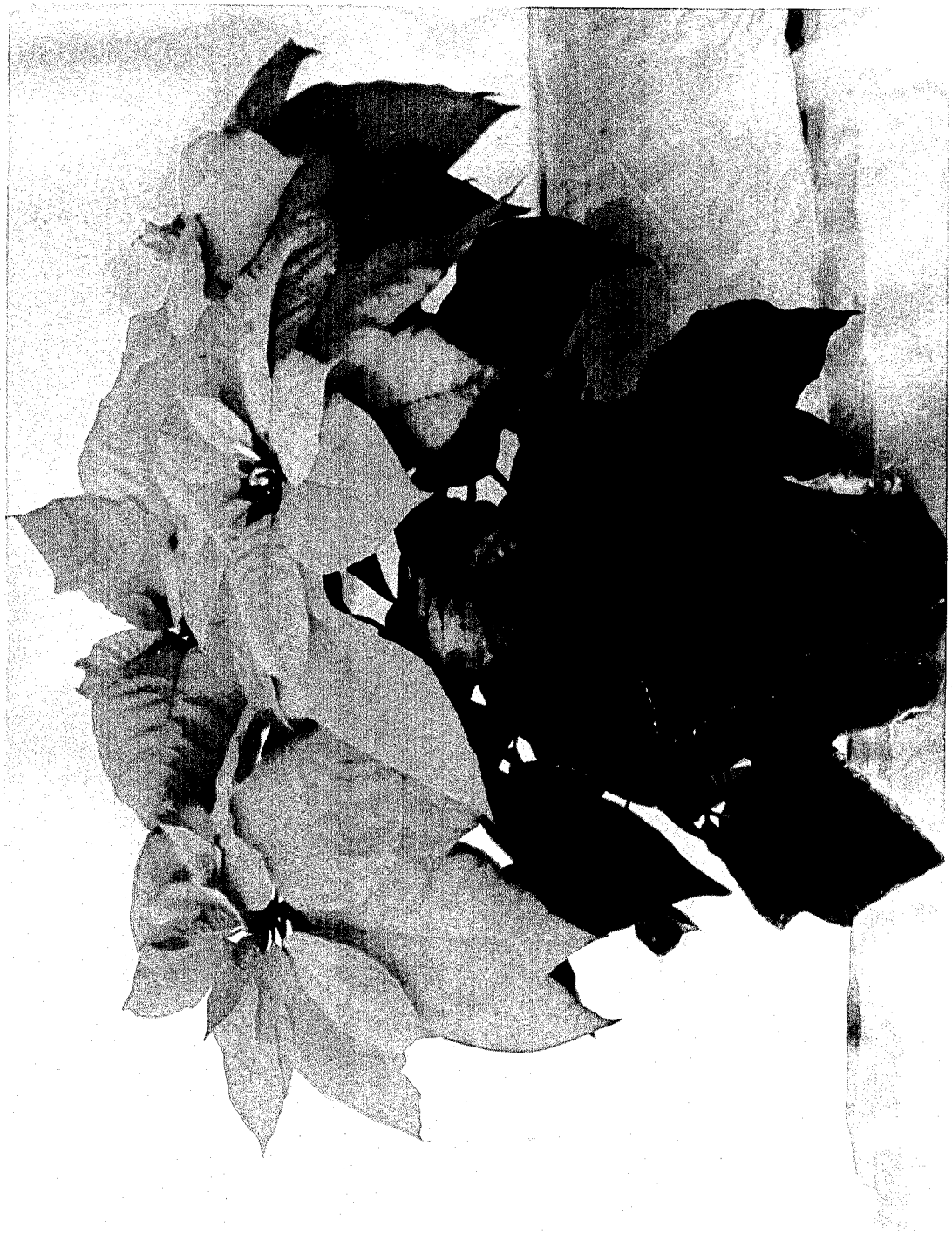

* * * * *